(12) United States Patent
Hansson

(10) Patent No.: US 8,372,125 B2
(45) Date of Patent: Feb. 12, 2013

(54) DEVICE FOR FIXATION OF A BONE FRACTURE

(76) Inventor: Henrik Hansson, Eriksberg (SE)

( * ) Notice: Subject to any disclaimer, the term of this patent is extended or adjusted under 35 U.S.C. 154(b) by 778 days.

(21) Appl. No.: 12/441,591

(22) PCT Filed: Sep. 18, 2007

(86) PCT No.: PCT/SE2007/000815
§ 371 (c)(1),
(2), (4) Date: Jul. 27, 2009

(87) PCT Pub. No.: WO2008/036016
PCT Pub. Date: Mar. 27, 2008

(65) Prior Publication Data
US 2009/0306726 A1    Dec. 10, 2009

(30) Foreign Application Priority Data
Sep. 21, 2006  (SE) .................................. 0601953

(51) Int. Cl.
*A61B 17/04*    (2006.01)
(52) U.S. Cl. .......................................... 606/301; 606/54
(58) Field of Classification Search .............. 606/54–57, 606/59
See application file for complete search history.

(56) References Cited

U.S. PATENT DOCUMENTS

| | | | |
|---|---|---|---|
| 1,556,966 A * | 10/1925 | Selig ................................ | 16/441 |
| 2,435,850 A * | 2/1948 | Siebrandt ......................... | 606/54 |
| 3,741,205 A | 6/1973 | Markolf et al. | |
| 4,444,179 A | 4/1984 | Trippi | |
| 4,564,007 A * | 1/1986 | Coombs et al. .................. | 606/59 |
| 4,838,252 A * | 6/1989 | Klaue ............................. | 606/280 |
| 5,741,251 A | 4/1998 | Benoist | |
| 6,238,417 B1 | 5/2001 | Cole | |
| 6,364,882 B1 * | 4/2002 | Orbay ........................... | 606/86 B |
| 6,663,630 B2 * | 12/2003 | Farley et al. ..................... | 606/54 |
| 2003/0050583 A1 | 3/2003 | Farley et al. | |
| 2004/0210228 A1 * | 10/2004 | Hagert ............................. | 606/79 |

FOREIGN PATENT DOCUMENTS

| | | |
|---|---|---|
| EP | 0450075 | 10/1991 |
| JP | 8-502662 | 3/1996 |

(Continued)

*Primary Examiner* — Nicholas Woodall
(74) *Attorney, Agent, or Firm* — Tarolli, Sundheim, Covell & Tummino LLP

(57) ABSTRACT

The present invention relates to a device for fixation of a bone fracture. The device comprises at least one appliance (1) for placing close to the bone fracture, and fixing elements in the form of pins (2) which are intended to be locked to the appliance (i) in order to fix the bone fracture (3). With the object of allowing correct positioning of the appliance and pins and thereafter driving the pins into correct positions for optimum stable fixation of the bone fracture, the appliance (1) is provided with predrilled holes (4) whose diameter is adapted to the diameter of forward portions (2a) of the pins (2) so that said forward portions can be inserted through the holes until they come up against the bone (3) with the fracture (3a) on which the appliance is used, which pins (2) have, to the rear of said forward portions (2a), threaded portions (2b) in which the outside diameter of the threads is larger than the diameter of said forward portions, and the material of which the appliance (1) is made is such that the threaded rear portions (2b) of the pins (2) can be screwed into it and the forward portions (2a) of the pins can thereby be driven into the bone (3) with the fracture (3a) on both sides of the fracture.

23 Claims, 2 Drawing Sheets

FOREIGN PATENT DOCUMENTS

| WO | 99/55248 | 11/1999 |
| WO | WO 99/55248 A1 | 11/1999 |
| WO | 03/037197 | 5/2003 |
| WO | WO 03/037197 A1 | 5/2003 |
| WO | 2006/013624 | 2/2006 |
| WO | 2006/013670 | 2/2006 |

* cited by examiner

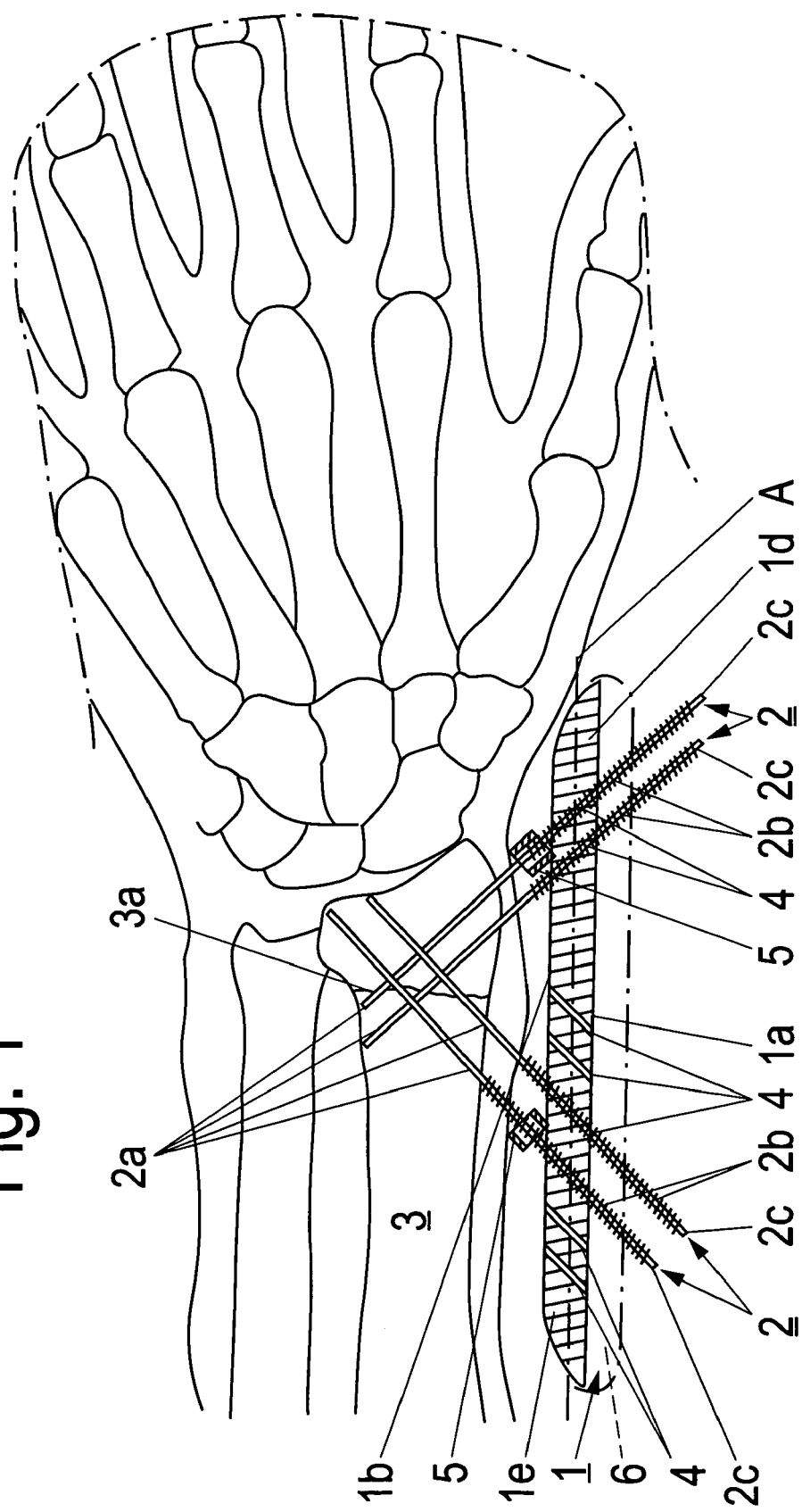

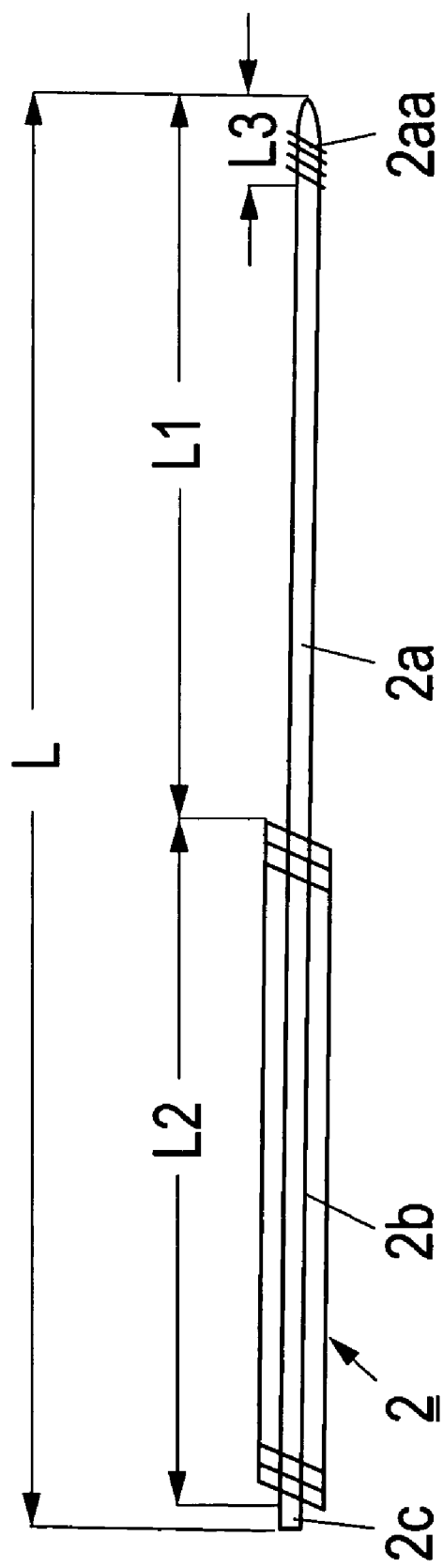

DEVICE FOR FIXATION OF A BONE FRACTURE

Field of the Invention

The present invention relates to a device for fixation of a bone fracture. The device comprises at least one appliance for placing close to the bone fracture, and fixing elements in the form of so-called pins intended to be locked to the appliance in order to fix the bone fracture.

BACKGROUND OF THE INVENTION

Known devices of this kind entail a relatively major surgical procedure and/or incisions at various different points during surgery. The procedure takes time and it may be difficult to position the device correctly relative to the fracture. Known fixation devices also frequently give the fracture insufficient stability for optimum healing.

SUMMARY OF THE INVENTION

The object of the present invention is to eliminate the aforesaid disadvantages of the state of the art. The device according to the invention is characterized accordingly in that the appliance is provided with predrilled holes with diameter adapted to the diameter of the forward portions of the pins so that said forward portions can be inserted through the holes until they come up against the fractured bone on which the appliance is used, that the pins have, to the rear of said forward portions, threaded portions in which the outside diameter of the threads is larger than the diameter of said forward portions, and that the material of which the appliance is made is such that the threaded rear portions of the pins can be screwed into it and the forward portions of the pins are thereby driven into the fractured bone on both sides of the fracture.

The device according to the invention comprises a small number of parts which are easy to apply. The configuration of these parts according to the invention makes it possible to place the appliance and the pins in a kind of (temporary) state of readiness in which the pins are known to be abutting correctly against the fractured bone before they are driven into their correct position therein. This makes the operating procedure easy to carry out; one incision is sufficient and the pins can be positioned in such a way as to achieve very stable fixation of the fracture. With the device according to the invention it is also possible to fix bone fractures of various kinds.

BRIEF DESCRIPTION OF THE DRAWINGS

The foregoing and other features characterizing the invention are described in more detail below with reference to the attached drawings, in which:

FIG. 1 is a schematic section depicting a device according to the invention for fixation of a radial fracture; and FIG. 2 is a schematic sideview illustrating a pin pertaining to the device according to the invention.

Description of Example Embodiments

As already indicated, the device according to the invention comprises at least one appliance 1 and fixing elements in the form of so-called pins 2 which are intended to be locked to the appliance in order to fix a fracture 3a in a bone 3. Fractures relevant here comprise inter alia collarbone fractures, upper arm fractures, elbow joint fractures, finger fractures and wrist fractures, e.g. a radial fracture as in FIG. 1.

The appliance 1 is of elongate, substantially platelike shape and size optimally suited to the intended application and is preferably made of polyethylene, e.g. UHMWPE (ultra high molecular weight polyethylene), in order by frictional locking to help to lock the pins 2 to the appliance, and because this material is transparent to radiography. Other materials may nevertheless be used, provided that they have the properties desired for the purpose. Since the appliance is of little weight (about 15 g) and small height, the device is easy to carry. In cross-section, the appliance 1 is of mainly truncated conical shape with four sides running in its longitudinal direction, comprising a side 1a which faces away from the bone 3 with the fracture 3a when the appliance is applied, a side 1b which faces towards the fractured bone and two side surfaces (not depicted) converging towards the side which faces towards the fractured bone in order to facilitate access to the operation site.

The appliance 1 is provided with predrilled holes 4 whose diameter is adapted to the diameter of forward portions 2a of the pins 2 so that said forward portions can be inserted through the holes until they come up against the bone 3 with the fracture 3a on which the appliance is used. The diameter of the holes 4 is equal to or somewhat larger than the diameter of said forward portions 2a. To the rear of said forward portions 2a, each pin 2 has a threaded portion 2b. The outside diameter of the threads on the threaded rear portion 2b is larger than the diameter of said forward portions 2a. The threaded rear portion 2b of the pins 2 can be screwed into the appliance 1, thereby either cutting threads in cases where the holes 4 in the appliance have no threads or cooperating with threads provided in the holes and adapted to the threads on the threaded rear portions 2b of the pins 2. This screwing in drives the forward portions 2a of the pins 2 into the bone 3 with the fracture 3a on both sides of the fracture for stable fixation of the latter.

The length L1 of the forward portions 2a of the pins 2 is such that they can be inserted through the holes 4 in the appliance 1 until they come up against the bone 3 with the fracture 3a without the threaded rear portions 2b of the pins intended to be screwed into the appliance having to be screwed into it. Inserting the forward portions 2a thus becomes easier. The length L1 of the forward portions 2a of the pins 2 is preferably such that when they come up against the bone 3 with the fracture 3a the threaded rear portions 2b of the pins come into contact simultaneously with the appliance 1. From this state of readiness it is possible to immediately start driving the forward portions 2a of the pins 2 into the bone 3 with the fracture 3a by screwing the rear portions 2b of the pins into the appliance 1. The length L1 of the forward portions 2a of the pins 2 is also such that they can be driven into the bone 3 with the fracture 3a as far as is necessary for stable fixation of the fracture without the threaded rear portions 2b, after being screwed into the appliance, being also screwed into the fractured bone. There is therefore no debris due to screwing into the bone 3 with the fracture 3a.

To the rear of the threaded rear portion 2b, each pin 2 also has with advantage a control portion 2c which preferably has no threads. This control portion 2c is of preferably the same diameter as the forward portion 2a.

In the depicted preferred embodiment of the device according to the invention for fixation of a radial fracture 3, the forward portion 2a of each pin 2 has preferably a length L1 of about 55 mm and a diameter of about 2 mm. The thread diameter on the threaded rear portion 2b is with advantage 2.4-2.5 mm. The threads run along a length L2 which is preferably likewise about 55 mm. The remainder of the length L of the pin comprises the relatively much shorter control portion 2c. The pins 2 are preferably made of stainless steel.

In the preferred embodiment, the diameter of the holes 4 in the appliance 1 is about 2.1 mm.

In the depicted preferred embodiment of the device, the elongate appliance 1 has at least two, with advantage two or three, predrilled holes 4 in a distal end portion 1d of the appliance and at least two, preferably four to six, predrilled holes 4 in a proximal end portion 1e of the appliance. At least two pins 2 are inserted through the holes 4 in the distal end portion 1d of the appliance 1 and likewise at least two pins 2 through the holes 4 in the proximal end portion 1e.

For the fixation of a radial fracture 3a in the depicted preferred embodiment, the predrilled holes 4 are oblique relative to an axis A of the appliance which runs in the longitudinal direction of the appliance 1, so that the pins 2 inserted through holes in the distal end portion 1d of the appliance cross the pins 2 inserted through holes in the proximal end portion 1e of the appliance. The pins 2 crossing each other in this way results in stable fixation of the fracture 3a and in a structure which prevents the appliance 1 from becoming detached and the pins 2 from moving outwards. The predrilled holes 4 are with advantage oblique, substantially at a 45° angle, relative to said longitudinal axis A of the appliance 1, so that the pins 2 inserted through holes 4 in the distal end portion 1d of the appliance cross substantially at right angles the pins 2 inserted through holes 4 in the proximal end portion of the appliance. The pins 2 thus form a quadrilateral, preferably substantially square, geometrical figure transverse to the longitudinal direction of the pins, resulting in further improvement of the fixation of the fracture 3a. Alternatively, the predrilled holes 4 may be oblique at different angles relative to the longitudinal axis A. The predrilled holes 4 in the distal end portion 1d may for example be oblique, substantially at 45°, relative to the longitudinal axis A, while the holes 4 in the proximal end portion 1e are oblique at an angle of between 45° and 60° relative to said axis. Accordingly, and this is also preferable, the predrilled holes 4 in the respective end portions 1d and 1e run substantially parallel with one another.

To achieve maximum stability in the fixation of the fracture 3a, the predrilled holes 4 are oblique relative to the longitudinal axis A of the appliance 1 so that all the pins 2 inserted through holes in the appliance's distal end portion 1d and proximal end portion 1e cross the fracture 3a. Preferably, at least one of the distal pins 2 and at least one of the pins 2 cross substantially the center of the fracture 3a.

An example of how the fixation of a fracture 3a, particularly a fracture in the radius 3, can be accomplished by means of the device described above is briefly described below:

Before the incision is made, the appliance 1 is placed in a correct position relative to the fracture 3a, i.e. the appliance is placed running in the longitudinal direction transversely across the fracture, and the particular predrilled holes 4 in the appliance which are to be used are determined. The fracture 3a is stabilized in a suitable manner and an incision of about 40-50 mm is made at a given point relative to the fracture. The forward portion 2a of a first distal pin 2 is inserted into a hole 4 intended for the purpose in the distal end portion 1d of the appliance 1 until it is felt that the tip portion 2aa of the pin has reached the radius 3, i.e. until a kind of state of readiness had been reached. This is done without the threaded rear portion 2b having to be screwed into the appliance 1, but the threaded rear portion 2b will now preferably be in contact with the side 1a of the appliance 1 which faces away from the bone 3 with the fracture 3a, around the hole 4 into which the distal pin 2 has been inserted. The appliance 1 will now serve as a kind of drilling guide and it is possible to use a pin 2 with correctly adapted length as above of the portions 2a, 2b to begin, by means of the control portion 2c, to screw the threaded rear portion 2b of the pin into the appliance, whereby the forward portion 2a of the pin is driven into the radius 3 on the distal side of the fracture 3a and continues through the fracture and proceeds into the bone on the proximal side of the fracture. The driving in may be facilitated if the tip portion 2aa of the forward portion 2a is also threaded. The length L3 of this possible threading may for example be a few millimeters. The screwing in continues with advantage until the tip portion 2aa penetrates the far cortex (far relative to the fixation device) of the radius 3, which takes place before the threaded rear portion 2b comes into contact with the bone. The whole process is monitored by radiography. It is important that the appliance 1 is kept parallel with the longitudinal axis of the bone 3 during the screwing in. It is also important that the appliance 1 is constantly kept at the intended distance from the bone 3, e.g. 10 mm, so that the operation site can be kept clean during the operation. This can be achieved by means, for example, of spacers 5 which may be applied to the respective pins 2 between the bone 3 and the fracture 3a and the side 1b of the appliance which faces towards the fractured bone, preferably at least the first distal pin 2 and the subsequent first proximal pin 2. The spacers 5 are releasable from the respective pin 2, e.g. by drawing them away from it sideways. Each spacer 5 has with advantage for this purpose a groove (not depicted) running in its longitudinal direction.

After any necessary adjustment proximally of the appliance 1, the first proximal pin 2 is driven into the radius 3 on the proximal side of the fracture 3a and proceeds through the fracture and the bone on the distal side of the fracture, crossing the first distal pin 2. The above procedure for driving in and fixing the distal pin is substantially repeated but preferably without the proximal pin 2 penetrating the far cortex (further relative to the fixation device) of the radius 3.

The insertion and fixing of a second distal pin 2 and a second proximal pin 2 in suitable holes 4 intended for the purpose in the appliance 1 and the driving of said pins into the radius 3 are performed in the same manner as above, resulting in stable fixation of the fracture 3a in the radius 3.

When all the pins 2 have been applied correctly and the fracture 3a has been stably fixed, the portions 2b, 2c of the pins which continue to protrude from the side 1a of the appliance 1 which faces away from the bone 3 with the fracture 3a are cut off as close to said side as possible. A protection 6 will with advantage be applied over the portions of the pins 2 which still protrude after the cutting. The protection may take the form of a cover 6, as indicated in FIG. 1, which is applied, e.g. by screwing or snapping firmly onto the appliance 1, so that the cover covers the side 1a of the appliance which faces away from the bone 3 with the fracture 3a. Screwholes made beforehand in the cover 6 and on the side 1a of the appliance 1 which faces away from the bone 3 with the fracture 3a make it easier to apply the cover by screwing it firmly on. The protection may also take the form of rubber caps (not depicted) placed on said portions of the pins 2 which still protrude after the cutting.

The operation is completed by the surgical wound being sewn up and bandaged.

It will be obvious to one skilled in the art that the device according to the invention can be altered and modified within the scopes of the claims set out below without departing from the idea and object of the invention. Thus, as indicated above, the shape and size of the device and its constituent parts may vary depending on how the device is to be used, i.e. what type of fracture is concerned, whether the patient is a child or an adult, how many pins are to be used and at what angle relative to the fracture, etc. The choice of material for the various parts of the device may also vary.

The invention claimed is:

1. A device for fixation of a bone fracture, which device comprises at least one appliance (1) for placing close to the bone fracture (3a) and fixing elements in the form of pins (2) which are intended to be locked to the appliance (1) in order to fix the bone fracture (3a), the appliance (1) including at least two predrilled holes (4) in a distal end portion (1d) of the appliance (1) and at least two predrilled holes (4) in a proximal end portion (1e) of the appliance (1) for insertion of the pins (2) through the holes (4) in the appliance (1), and the predrilled holes (4) being oblique relative to a longitudinal axis (A) of the appliance (1) such that, after placing the appliance (1) running in the longitudinal direction transversely across the bone fracture (3a), the pins (2) which are inserted through the holes (4) in the distal end portion (1d) of the appliance (1) are adapted to be driven into a bone fragment on a distal side of the bone fracture (3a), through the bone fracture (3a) and into a bone fragment on a proximal side of the bone fracture (3a), and such that the pins which are inserted through the holes (4) in the proximal end portion (1e) of the appliance (1) are adapted to be driven into the bone fragment on the proximal side of the bone fracture (3a), through the bone fracture (3a) and into the bone fragment on the distal side of the bone fracture (3a), and such that pins (2) inserted through holes in the distal end portion (1d) of the appliance cross pins (2) inserted through holes in the proximal end portion (1e) of the appliance, thereby forming a substantially quadrilateral figure transverse to the longitudinal direction of the pins (2).

2. A device according to claim 1, wherein a tip portion (2aa) of forward portions (2a) of the pins (2) is threaded.

3. A device according to claim 1, wherein the appliance (1) is made of polyethylene.

4. A device according to claim 1, intended for the fixation of primarily radial fractures, wherein the predrilled holes (4) are oblique relative to a longitudinal axis (A) of the appliance (1), with the result that pins (2) inserted through holes in the distal end portion (1d) of the appliance cross pins (2) inserted through holes in the proximal end portion (1e) of the appliance.

5. A device according to claim 4, wherein the predrilled holes (4) are oblique, at a 45° angle relative to a longitudinal axis (A) of the appliance (1), with the result that pins (2) inserted through holes in the distal end portion (1d) of the appliance cross pins (2) inserted through holes in the proximal end portion (1e) of the appliance at right angles thereby forming a square figure.

6. A device according to claim 4, wherein the predrilled holes (4) are oblique at various different angles relative to a longitudinal axis (A) of the appliance (1).

7. A device according to claim 1, wherein the predrilled holes (4) in the respective end portions (1d, 1e) of the appliance (1) run substantially parallel with one another.

8. A device according to claim 1, wherein at least one of the distal pins (2) and at least one of the proximal pins (2) are adapted to cross substantially the center of the fracture (3a).

9. A device according to claim 1, wherein a protection (6) may be placed over portions of the pins (2) which, after cutting of the pins, protrude from the side (1a) of the appliance (1) which faces away from the bone (3) with the fracture (3a).

10. A device according to claim 9, wherein the protection takes the form of a cover (6) which may be applied to the appliance (1) and which covers the side (1a) of the appliance which faces away from the bone (3) with the fracture (3a).

11. A device according to claim 10, wherein the cover (6) may be screwed firmly to the appliance (1).

12. A device according to claim 9, wherein the protection takes the form of rubber caps placed on the portions of the pins (2) which, after cutting of the pins, protrude from the side (1a) of the appliance (1) which faces away from the bone (3) with the fracture (3a).

13. A device according to claim 1, wherein spacers (5) may be placed on the pins (2) between the bone (3) with the fracture (3a) and the side (1b) of the appliance (1) which faces towards the fractured bone.

14. A device according to claim 13, wherein the spacers (5) are removable.

15. A device according to claim 1, wherein the predrilled holes (4) provided in the appliance (1) have a diameter which is adapted to the diameter of forward portions (2a) of the pins (2) so that said forward portions can be inserted through the holes until they come up against the bone (3) with the fracture (3a) on which the appliance is used, the pins (2) have, to the rear of said forward portions (2a), threaded portions (2b) in which the outside diameter of the threads is larger than the diameter of said forward portions, and the material of which the appliance (1) is made is such that the threaded rear portions (2b) of the pins (2) can be screwed into it and the forward portions (2a) of the pins are thereby driven into the bone (3) with the fracture (3a) on both sides of the fracture.

16. A device according to claim 15, wherein the length (L1) of the forward portions (2a) of the pins (2) is such that they can be inserted through the holes (4) in the appliance (1) until they come up against the bone (3) with the fracture (3a) without the threaded rear portions (2b) of the pins having to be screwed into the appliance.

17. A device according to claim 15, wherein the length (L1) of the forward portions (2a) of the pins (2) is such that when said forward portions (2a) come up against the bone (3) with the fracture (3a), the threaded rear portions (2b) of the pins come simultaneously into contact with the appliance (1).

18. A device according to claim 15, wherein the length (L1) of the forward portions (2a) of the pins (2) is such they can be driven into the bone (3) with the fracture (3a) without the threaded rear portions (2b) of the pins having to be screwed therein.

19. A device according to claim 15, wherein the predrilled holes (4) in the appliance (1) have no threads and that the threaded rear portions (2b) of the pins (2) cut threads into the appliance when said threaded rear portions are screwed into it.

20. A device according to claim 15, wherein the predrilled holes (4) in the appliance (1) have threads adapted to the threads on the threaded rear portions (2b) of the pins (2).

21. A device according to claim 15, wherein the appliance (1) has in cross-section a substantially truncated conical shape.

22. A device for fixation of a bone fracture, which device comprises at least one appliance (1) for placing close to the bone fracture (3a) and fixing elements in the form of pins (2) which are intended to be locked to the appliance (1) in order to fix the bone fracture (3a), wherein:

the appliance (1) is provided with predrilled holes (4) whose diameter is adapted to the diameter of forward portions (2a) of the pins (2) so that said forward portions can be inserted through the holes until they come up against the bone (3) with the fracture (3a) on which the appliance is used, the pins (2) have, to the rear of said forward portions (2a), threaded portions (2b) in which the outside diameter of the threads is larger than the diameter of said forward portions, and the material of which the appliance (1) is made is such that the threaded rear portions (2b) of the pins (2) can be screwed into it and the forward portions (2a) of the pins are thereby driven into the bone (3) with the fracture (3a) on both sides of the fracture, and the predrilled holes (4) in the appliance (1) have no threads and that the threaded rear portions (2b) of the pins (2) cut threads into the appliance when said threaded rear portions are screwed into it.

23. A device for fixation of a bone fracture, which device comprises at least one appliance (1) for placing close to the bone fracture (3a) and fixing elements in the form of pins (2) which are intended to be locked to the appliance (1) in order to fix the bone fracture (3a), wherein:

the appliance (1) is provided with predrilled holes (4) whose diameter is adapted to the diameter of forward portions (2a) of the pins (2) so that said forward portions can be inserted through the holes until they come up against the bone (3) with the fracture (3a) on which the appliance is used, the pins (2) have, to the rear of said forward portions (2a), threaded portions (2b) in which the outside diameter of the threads is larger than the diameter of said forward portions, and the material of which the appliance (1) is made is such that the threaded rear portions (2b) of the pins (2) can be screwed into it and the forward portions (2a) of the pins are thereby driven into the bone (3) with the fracture (3a) on both sides of the fracture, the appliance (1) including at least two predrilled holes (4) in a distal end portion (1d) of the appliance (1) and at least two predrilled holes (4) in a proximal end portion (1e) of the appliance (1) for insertion of the pins (2) through the holes (4) in the appliance (1), the predrilled holes (4) are oblique relative to a longitudinal axis (A) of the appliance (1), with the result that pins (2) inserted through holes in the distal end portion (1d) of the appliance cross pins (2) inserted through holes in the proximal end portion (1e) of the appliance, and the predrilled holes (4) are oblique, substantially at a 45° angle, relative to a longitudinal axis (A) of the appliance (1), with the result that pins (2) inserted through holes in the distal end portion (1d) of the appliance cross pins (2) inserted through holes in the proximal end portion (1e) of the appliance, substantially at right angles, thereby forming a substantially quadrilateral, preferably square, figure.

* * * * *